United States Patent
Hacker et al.

(10) Patent No.: US 7,077,845 B2
(45) Date of Patent: Jul. 18, 2006

(54) SURGICAL ABRADER WITH SUCTION PORT PROXIMAL TO BEARING

(75) Inventors: Randall L. Hacker, Naples, FL (US); John W. Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 49 days.

(21) Appl. No.: 10/796,988

(22) Filed: Mar. 11, 2004

(65) Prior Publication Data
US 2004/0181251 A1    Sep. 16, 2004

Related U.S. Application Data

(60) Provisional application No. 60/453,196, filed on Mar. 11, 2003.

(51) Int. Cl.
*A61B 17/00*    (2006.01)

(52) U.S. Cl. .......................... 606/80; 606/180

(58) Field of Classification Search ........... 606/53, 606/79, 80, 159, 167, 170, 171, 185, 180; 607/19, 22, 35
See application file for complete search history.

(56) References Cited

U.S. PATENT DOCUMENTS

| | | | | |
|---|---|---|---|---|
| 4,842,578 A | * | 6/1989 | Johnson et al. | 604/22 |
| 5,913,867 A | * | 6/1999 | Dion | 606/180 |
| 5,922,003 A | * | 7/1999 | Anctil et al. | 606/170 |
| 6,053,923 A | * | 4/2000 | Veca et al. | 606/80 |
| 2003/0055404 A1 | | 3/2003 | Moustafis | |

* cited by examiner

*Primary Examiner*—Glenn K. Dawson
(74) *Attorney, Agent, or Firm*—Dickstein Shapiro Morin & Oshinsky LLP

(57) ABSTRACT

An apparatus for abrading tissue includes a bearing tube having distal and proximal ends, and a suction port formed distally in a sidewall of the bearing tube. An inner tube disposed within the bearing tube has a distal opening, the distal opening being located proximal of the suction port in the sidewall of the bearing tube. A solid transition region extending distally from the inner tube is disposed distal to the distal opening. An abrading element supported distally by the solid transition region is used to perform orthopedic abrading procedures. The outer diameter of the abrading element is greater than the inner diameter of the bearing tube. Debris generated by abrading procedures is aspirated through the suction port formed in the sidewall of the bearing tube and into the lumen of the inner tube. A hooded sheath extends distally from the bearing tube, or optionally from a sheath tube provided over the bearing tube.

14 Claims, 4 Drawing Sheets

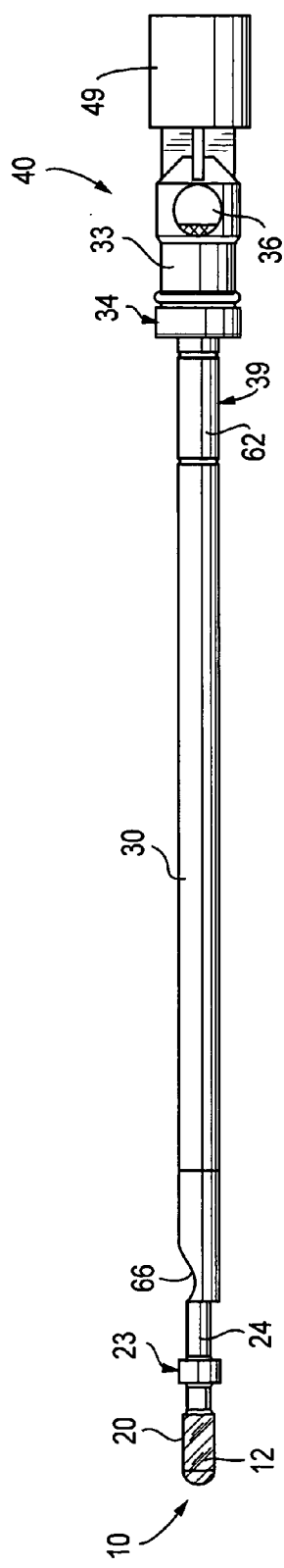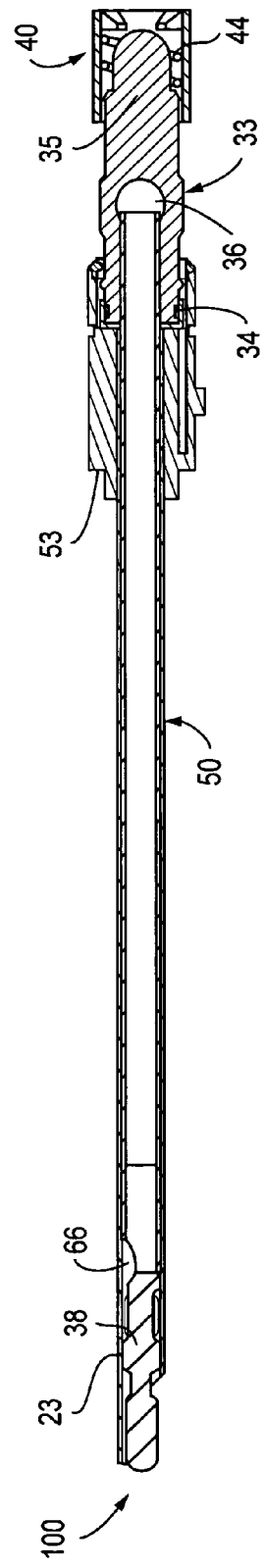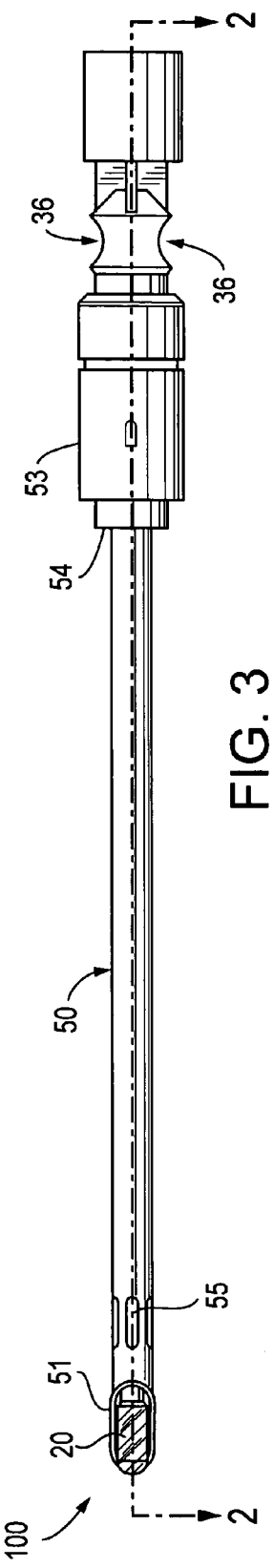

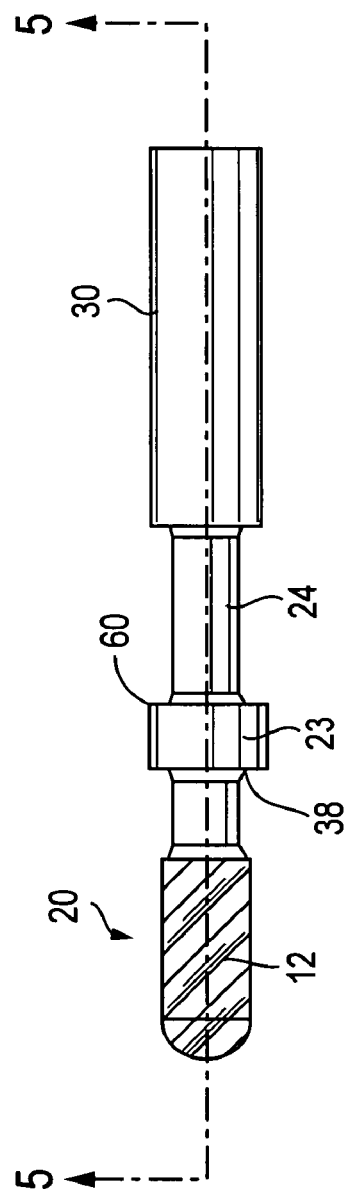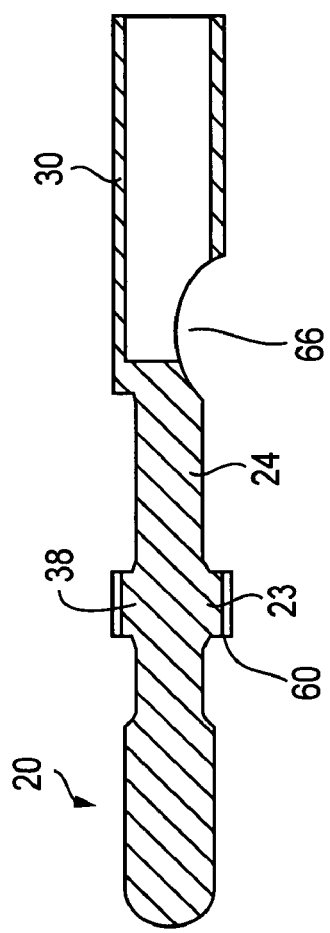
FIG. 4
FIG. 5

SURGICAL ABRADER WITH SUCTION PORT PROXIMAL TO BEARING

This application claims the benefit of U.S. Provisional Application No. 60/453,196, filed Mar. 11, 2003.

FIELD OF THE INVENTION

The present invention relates to the field of surgery and, more particularly, to methods and instruments for abrading tissue during arthroscopic procedures.

BACKGROUND OF THE INVENTION

Methods and surgical instruments for abrading tissue are known in the art. Typically, surgical abrading instruments are sized and shaped to be inserted into the body through a small opening in the flesh, as would be used in arthroscopic surgical procedures. U.S. Pat. No. 4,842,578 to Johnson et al. discloses a surgical abrading instrument that includes the combination of a distally, side-supported inner drive tube carrying on its end an abrading element, and a fixed bearing tube surrounding the inner tube and providing at a bearing region the distal support for the inner tube. A distal extension of the bearing tube provides a sheath for a portion of the abrading element. A vacuum passage communicates proximally from the region of the abrading element, past the bearing region, to a proximal vacuum connection. During driving of the tube and drawing of suction through the vacuum connection, particles dislodged by the driven, side-supported abrading element may be drawn past the bearing region and out of the instrument.

Once inserted into the body, the abrader is used for various surgical procedures that involve abrading, cutting, or shaping soft tissue and hard tissue, such as bone, cartilage, or ligament, by use of a rotating abrading head secured to a rotatable inner tube. As the tissue is being abraded, debris is generally drawn by suction through the lumen of the rotatable inner tube, along with physiological and irrigation fluid. In the example disclosed in the '578 patent, the suction port is located immediately proximal to the abrading head, and a bearing is located proximal to the head and the suction port to allow maximum exposure of the abrading head at the distal tip of the instrument. According to the '578 patent, the debris flows past the abrading head and enters the immediately adjacent suction port between the inner tube and the outer tube. During the abrading procedure, tissue may wrap around the instrument and block the suction port.

Another approach is provided in U.S. Pat. No. 6,053,923 issued to Veca et al. The abrading instrument of the '923 patent has openings in the side of the rotating inner tube, which align with a single suction port in the side of the outer tubular member. The openings in the inner tube are disposed proximally to the abrading head. Thus, surgical debris is drawn back from the abrading head along the outside of the bearing area, and then into the suction port of the outer tube, through the suction openings of the inner tube, and out of the instrument. A self-cleaning mechanism is formed by sharpening the edges of the two openings, which pass at close tolerances during rotation of the inner tube within the outer tube, to impart a tissue-cutting action as the edges of the openings pass one another.

A surgeon using the abrading apparatus disclosed in the '923 patent must be careful, however, to avoid cutting tissue adjacent the surgical site with the sharpened edges of the self-cleaning mechanism. Further, tight tolerances between the inner and outer tubes necessary to provide an effective tissue-cutting action also render the instrument vulnerable to binding between the inner and outer tubes during an abrading operation. In addition, as the inner tube rotates within the outer tube, the suction flow through the ports in the outer and inner tubes becomes at least partially blocked or impeded by portions of the inner tube cyclically closing off the openings as the inner tube rotates. Thus, an improved design for avoiding aspiration of tissue through abrading apparatus bearings and improving aspiration flow is desired.

Accordingly, it would be desirable to provide a surgical abrading instrument that reduces blockage and eliminates the need for repeatedly clearing the abrader. There also is a need for a method for conducting a surgical abrading procedure with increased efficiency and reduced cost and time.

SUMMARY OF THE INVENTION

The present invention overcomes the disadvantages of the prior art and fulfills the needs noted above by providing a surgical abrading instrument having an aspiration section that features a suction port disposed in an outer bearing tube of the instrument and proximal to a distal bearing which, in turn, is disposed proximal to an abrading head. Preferably, the suction port is in communication with a chamber formed between an inner tube and an abrading head. The chamber, in turn, is in communication with at least one opening in an inner hollow tube, to allow surgical debris produced by the abrading head to be drawn through the suction port as it is aspirated from the operative site into the inner hollow tube and out of the abrading instrument.

The bearing tube of the surgical abrading instrument surrounds the inner tube. An optional hood surrounds the inner tube, at least partially, to expose a rotary-driven abrading head, at least on one side. Cantilever support of the abrading head by a bearing disposed proximal to the abrading head allows maximum exposure of the abrading head at the distal end of the instrument. The suction port on the bearing tube is provided as a plurality of longitudinal slots disposed proximal to the distal bearing. The inner tube is hollow and has an opening through which tissue and debris produced by the abrading procedure are drawn. The tissue and debris from the operative site are drawn by suction into the hollow inner tube through an opening in the bearing tube. At least one opening in the bearing tube and the opening in the inner tube provide an unimpeded path for fluid and debris to be aspirated away from the surgical site without passing through the bearing that supports the abrading head. In addition, the present invention avoids rough edges and surfaces on which tissue potentially could become lodged, or around which tissue potentially could become wrapped and entangled.

Other features and advantages of the present invention will become apparent from the following description of the invention, which refers to the accompanying drawings.

BRIEF DESCRIPTION OF THE DRAWINGS

FIG. 1 illustrates a side elevation of an inner tube and abrading head of a surgical abrading instrument according to the present invention;

FIG. 2 illustrates a cross-sectional view, taken as indicated by line II—II of FIG. 3, of a surgical abrading instrument according to the present invention;

FIG. 3 illustrates a top plan view of a surgical abrading instrument according to the present invention;

FIG. 4 illustrates a detailed view of the abrading head of FIG. 1;

FIG. 5 illustrates a detailed cross-sectional view of the abrading head of FIG. 1, taken as indicated by line V—V of FIG. 4;

DETAILED DESCRIPTION OF THE PREFERRED EMBODIMENTS

Figure 6:
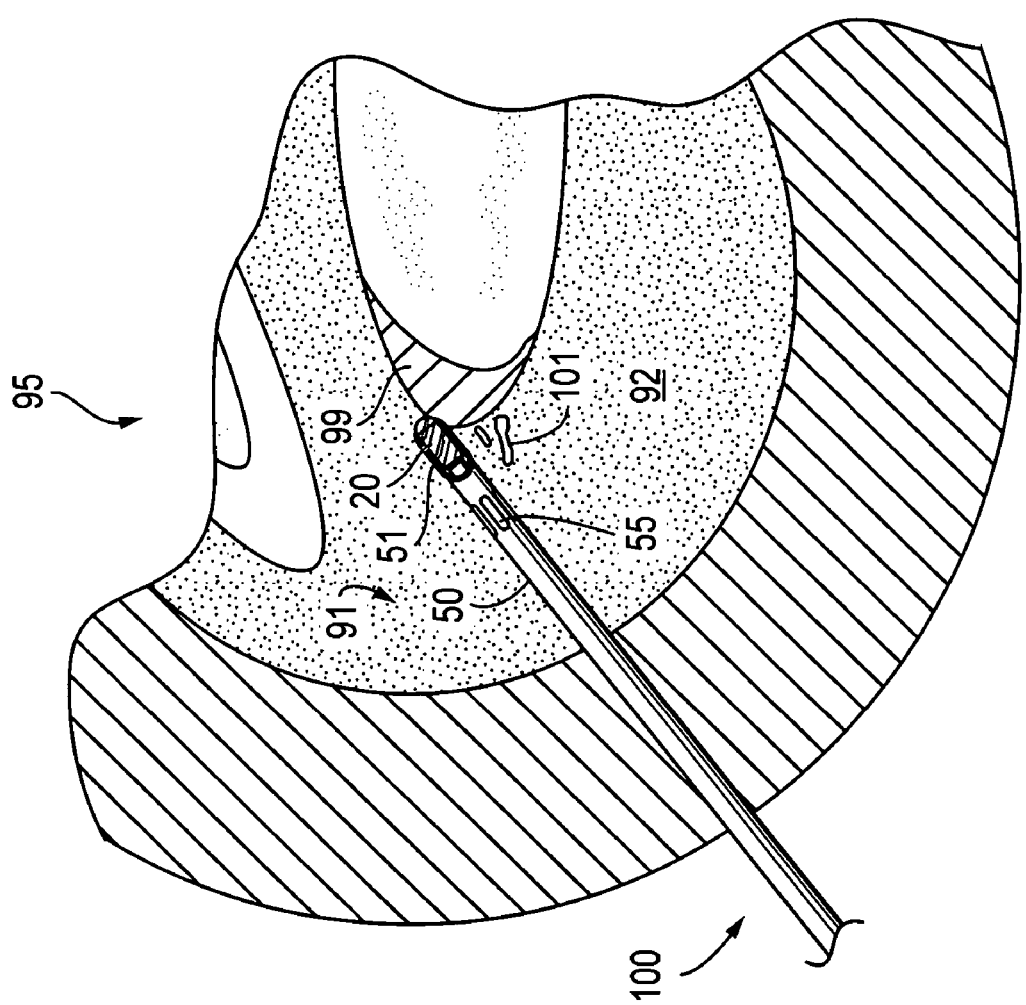
FIG. 6 illustrates a schematic cross-sectional view of a knee joint region undergoing an abrading procedure according to the present invention.

The present invention provides a surgical abrading instrument configured to reduce blockage of the instrument and eliminate the need for manually clearing the abrader. The surgical abrading instrument of the present invention includes a suction region disposed in an outer bearing tube of the instrument and proximal to a distal bearing, which, in turn, is disposed proximal to an abrading head. The suction region is in communication with an opening leading to the lumen of an inner tube. Debris produced during the abrading procedure is drawn by aspiration from the operative site through the suction region of the bearing tube and into the hollow inner tube.

Referring now to the drawings, where like elements are designated by like reference numerals, FIG. 1 illustrates an inner tube assembly 10 of a surgical abrading instrument 100 (FIGS. 2–3) according to the present invention. Inner tube assembly 10 is adapted to rotate within a fixed bearing tube 50 (FIGS. 2–3). The inner tube assembly 10 is formed of a rotary-driven abrading head 20 securely attached to a hollow inner tube 30. The inner and outer diameters of inner tube 30 are substantially uniform, i.e., without taper.

Abrading head 20 is connected to inner tube 30 by a bearing assembly 23 and a solid transition region 24. Bearing assembly 23 fits precisely within bearing tube 50. Solid transition region 24 has a smaller diameter than bearing assembly 23 and the inside of bearing tube 50, forming an annular clearance around the solid transition region within bearing tube 50 and proximal to bearing assembly 23. The hollow inner tube 30 is provided with an opening 66 (FIGS. 1, 2, and 5) located at its distal end. Opening 66 is arranged to be in constant fluid communication with the clearance formed around solid transition region 24, and with openings 55 in bearing tube 50, discussed further below. As a result, an aspirating flow developed through openings 55 and opening 66 by suction applied through hollow inner tube 30 is unimpeded during operational rotation of inner tube 30.

The abrading head 20 features a plurality of helical cutting flutes 12, which are arranged so that the abrading head 20 cuts more aggressively in a forward (clockwise) rotational direction than in the opposite rotational direction. The abrading head 20 is elongated and cylindrical, as shown in FIGS. 1–5, or may have any other desirable size, shape or configuration, for example round, depending on the morphology and pathology of the tissue to be abraded. The abrading head 20 and the inner tube 30 are formed of stainless steel or aluminum, for example, or of a polymer material if a disposable tube assembly is desired.

The fixed bearing tube 50 of FIG. 3 optionally includes a tapered or angled shield 51, which tapers at an angle of about 45° to expose a portion of the abrading head 20. The bearing tube 50 is further provided with a plurality of longitudinal slots 55 disposed proximal to distal bearing 23 (FIG. 2).

Slots 55 can be provided in various shapes and configurations, in addition to the elongated, oval configuration with a length of about 8 to 10 millimeters and a width of about 2 to 3 millimeters, illustrated in FIG. 3. Slots 55 provide a passageway located proximally from the abrading head 20 for debris and pieces of bone or tissue produced by the abrading procedure, which are drawn by suction from the operative site through opening 66 of the hollow inner tube 30.

A drive assembly 40 is disposed on the distal end of the inner tube assembly 10. The drive assembly 40 is securely attached to the inner tube 30 within hub 33. The transition between inner tube 30 and hub 33 features a thrust washer 34, which provides an axial bearing surface between inner tube assembly 10 and bearing tube assembly 50. Hub 33 is engaged by a compression spring 44 disposed within spring retainer 49 to allow attachment of a driver that engages drive tab 35.

Aspiration access ports 36 are formed radially in hub 33 and communicate with the lumen of inner tube 30. A driver assembly provides suction through the aspiration access ports. An outer hub 53 provided with distal opening 54 is securely attached to the proximal end of the fixed bearing tube 50. The outer hub 53 is designed to fit over and engage the thrust washer 34.

The inner and outer diameters of bearing tube 50 are uniform. Bearings 23 and 39 allow the inner tube 30 and the abrading head 20 to maintain an axial position relative to the bearing tube 50 during rotation of the inner tube 30. Bearings 23 and 39 each are formed of a sleeve 60, 62 of a lubricious heat-shrink polyolefin tubing material (MT 2000, RayChem). Distal bearing 23 is formed by shrink-wrapping sleeve 60 over an enlarged portion 38 of solid transition region 24. Proximal bearing 39 features sleeve 62 disposed by shrink-wrapping a sleeve into a groove formed in inner tube 30.

To better illustrate an exemplary surgical procedure conducted with the abrader 100 of the present invention, reference is now made to FIG. 6, which illustrates a schematic cross-sectional view of a knee joint region 95. The knee joint region 95 of FIG. 6 may undergo orthopedic abrading as part of an arthroscopic surgical procedure, for example. As is known in the art, surgery is viewed using an arthroscope (not shown) introduced into knee cavity 92 (FIG. 6) in close proximity to target tissue 99.

Once abrading head 20 of the abrading instrument 100 is positioned in the proximity of the target tissue 99, the drive assembly 40 disposed at the distal end of the inner tube assembly 10 (FIGS. 1–2) is rotated. Helical cutting flutes 12 of the abrading head 20 are brought into engagement with the desired area of the target tissue 99 to be shaped. Debris 101 produced while shaping the desired area is drawn from the target tissue 99, through the longitudinal slots 55 of the bearing tube 50, into the opening 66 of the hollow inner tube 30, and along to the aspiration access ports 36 (FIGS. 2 and 3). As the debris 101 is aspirated away from the target tissue 99, the debris easily flows through the longitudinal slots 55 and into the hollow tube 30, without wrapping around the abrader, for example, or blocking the bearing 23 or spaces between the inner tube 10 and the bearing tube 50.

Figure 7:
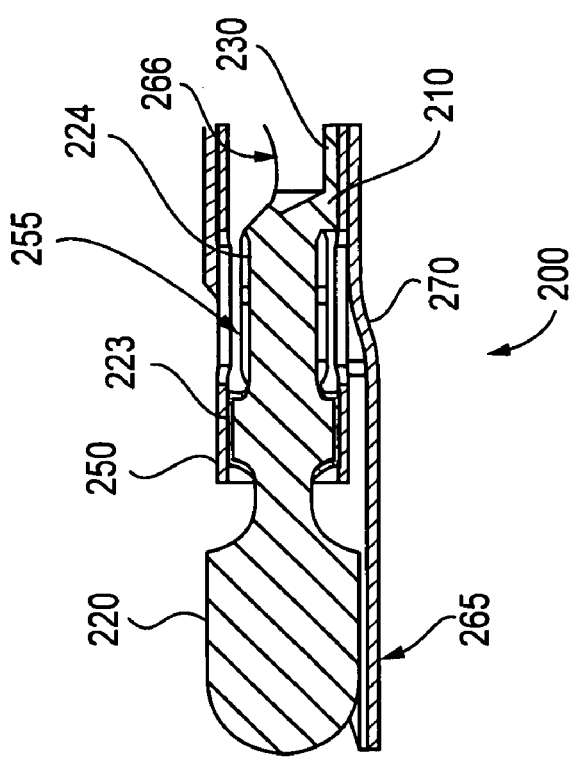
FIG. 7 is a cross-sectional view of the head of an abrading instrument according to an alternative embodiment of the present invention.
Figure 8:
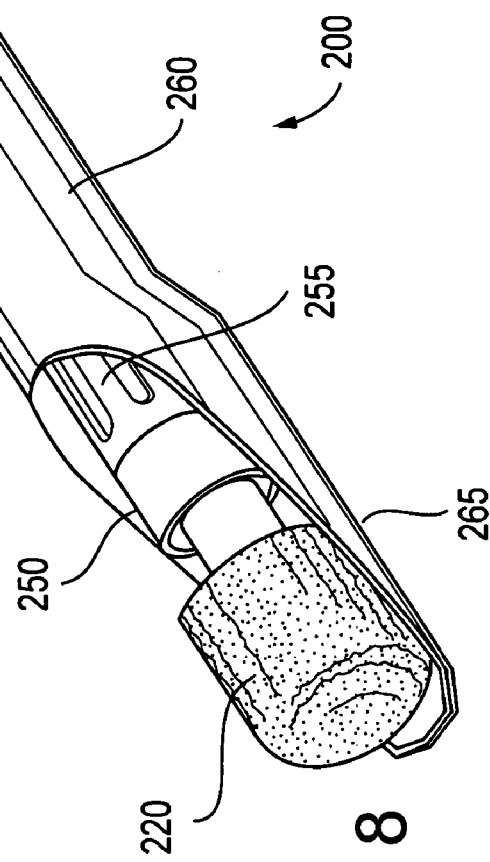
FIG. 8 is a perspective view of the head of the abrading instrument of FIG. 7.

FIGS. 7 and 8 illustrate features of an abrading instrument 200 according to an alternative embodiment of the present invention. Only a distal end of abrading instrument 200 is shown, remaining portions being similar to those of abrading instrument 100 described above. Abrader 200 includes an inner tube assembly 210 adapted to rotate within a fixed bearing tube 250. The inner tube assembly 210 includes a rotary-driven abrading head 220 securely attached to a hollow inner tube 230 by a bearing assembly 223, and a narrower solid transition region 224. The hollow inner tube 230 is provided with an opening 266 located distally on inner tube 230, and proximal to solid transition region 224. The formation of opening 266 on one side of inner tube 230 results in an unimpeded rotary application of aspiration as the inner tube spins within the bearing tube during operation.

A plurality of longitudinal slots 255 is formed in bearing tube 250 proximal of distal bearing 223. Slots 255 provide a passageway located proximal to the abrader head 220, through which debris and pieces of bone or tissue produced by the abrading procedure are aspirated, as described above. Abrader 200 further includes a sheath tube 260 having a tapered or angled hooded sheath 265 extending distally. Hooded sheath 265 partially surrounds abrading head 220 and has an inner diameter larger than the outer diameter of bearing tube 250, and larger than the outer diameter of abrading head 220, forming a clearance between abrading head 220 and hooded sheath 265. A tapered transition 270 formed between sheath tube 260 and hooded sheath 265 flares to a maximum diameter where it joins hooded sheath 265, preferably at a location axially proximal to bearing 223. The tapered transition 270 and hooded sheath 265 provide a clearance that allows direct fluid access to slots 255. An alternative arrangement replaces slots 255 with a single opening, formed in the bearing tube on a side facing toward hooded sheath 265. The hooded sheath 265 protects the opening from becoming blocked during surgery by intact tissue adjacent the operative site.

The outer diameter of abrading head 220 preferably extends radially beyond the inner diameter of the bearing tube 250, and preferably is at least equal to the outer diameter of bearing tube 250, and more preferably extends to the outer diameter of sheath tube 260. As a result, an outer surface of the instrument serves as a guide for the abrading head 220, and allows for application of a maximum surface area of the abrading head to the treatment surface, without angling the abrader. A maximized outer diameter of abrading head 220 can be provided readily in a disposable abrader, which is used once and does not require disassembly to be prepared for a subsequent surgery.

Although the present invention has been described in relation to particular embodiments thereof, many other variations and modifications and other uses will become apparent to those skilled in the art. It should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for abrading tissue, comprising:
a bearing tube having a distal end and a proximal end;
a suction port formed distally in a sidewall of the bearing tube, the suction port being spaced from the distal end of the bearing tube;
an inner tube disposed within the bearing tube and having a distal suction opening, the distal suction opening being located proximal of the suction port in the sidewall of the bearing tube;
a solid transition region extending distally from the inner tube and disposed distal to the distal suction opening;
a distal bearing sleeve disposed on the solid transition region extending distally from the inner tube; and
an abrading element disposed distally and supported on the solid transition region.

2. The apparatus of claim 1, wherein the solid transition region has an outer diameter smaller than an inner diameter of bearing tube to provide a clearance between the solid transition region and the bearing tube.

3. The apparatus of claim 2, wherein the distal suction opening is arranged operationally to be in constant fluid communication with the clearance.

4. The apparatus of claim 1, further comprising a proximal bearing sleeve disposed on the inner tube.

5. The apparatus of claim 1, wherein the solid transition region extending distally from the inner tube is attached to a support disposed adjacent the distal suction opening.

6. The apparatus of claim 1, wherein an outer diameter of the inner tube is uniform.

7. The apparatus of claim 1, wherein the inner diameter of the inner tube is uniform.

8. The apparatus of claim 1, further comprising a drive assembly attached to the proximal end of the inner tube.

9. The apparatus of claim 8, wherein the drive assembly includes suction ports extending radially, the suction ports connecting to a lumen of the inner tube.

10. The apparatus of claim 1, wherein the abrading element has an outer diameter substantially equal to an outer diameter of the bearing tube.

11. The apparatus of claim 1, further comprising a sheath tube in which the bearing tube is disposed, the sheath tube including a hooded sheath formed on a distal end and at least partially surrounding the abrading element.

12. A method of abrading tissue, comprising:
proximating tissue to be abraded with an abrading instrument, the abrading instrument including:
a bearing tube having a distal end and a proximal end, and a suction port formed distally in a sidewall of the bearing tube, the suction port being spaced from the distal end of the bearing tube;
an inner tube disposed within the bearing tube and having a distal suction opening, the distal suction opening being located proximal to the suction port in the sidewall of the bearing tube;
a solid transition region extending distally from the inner tube and disposed distal to the distal suction opening;
a distal bearing sleeve disposed on the solid transition region extending distally from the inner tube;
a proximal bearing sleeve disposed on the inner tube; and
an abrading element disposed distally on the solid transition region;
abrading the tissue with the abrading element; and
aspirating debris generating by abrading the tissue through the suction port and into the inner tube through the distal suction opening.

13. The method of claim 12, wherein the tissue to be abraded is in a knee.

14. The method of claim 12, wherein the abrading element is rotated.

* * * * *